Figure 1:
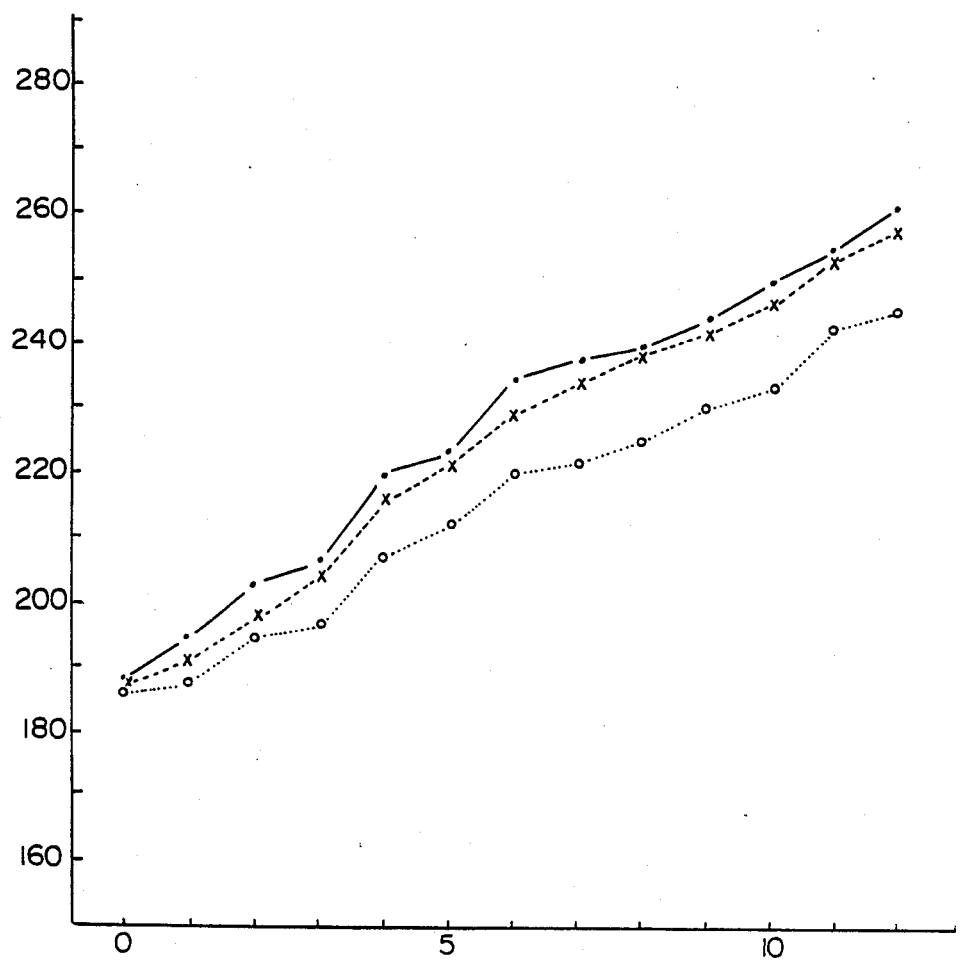

United States Patent [19]

Enomoto et al.

[11] Patent Number: 4,657,907

[45] Date of Patent: * Apr. 14, 1987

[54] LOW DOSAGE COMPOSITIONS OF FINELY PULVERIZED 2,4-DIAMINO-6-(2,5-DICHLOROPHENYL)-1,3,5-TRIAZINE AND PHARMACEUTICALLY ACCEPTABLE ACID ADDITION SALTS THEREOF AND ADMINISTRATION THEREOF

[75] Inventors: Hiroshi Enomoto, Magaokakyo; Masanobu Kawamata, Kyoto; Akira Nomura, Hirakata; Yoshiaki Aoyagi, Otsu; Fusao Ueda, Shige, all of Japan

[73] Assignee: Nippon Shinyaku Co., Ltd., Japan

[ * ] Notice: The portion of the term of this patent subsequent to Jul. 30, 2002 has been disclaimed.

[21] Appl. No.: 722,710

[22] Filed: Apr. 12, 1985

Related U.S. Application Data

[63] Continuation-in-part of Ser. No. 403,702, Jul. 3, 1982, Pat. No. 4,532,238.

[30] Foreign Application Priority Data

Aug. 4, 1981 [JP] Japan .................................. 56-122876

[51] Int. Cl.[4] .............................................. A61K 31/53
[52] U.S. Cl. ..................................................... 514/245
[58] Field of Search ........................................ 514/245

[56] References Cited

U.S. PATENT DOCUMENTS 3,966,728 6/1976 Murai et al. ......................... 544/206

Primary Examiner—Frederick E. Waddell
Attorney, Agent, or Firm—Jacobs & Jacobs

[57] ABSTRACT 2,4-diamino-6-(2,5-dichlorophenyl)-1,3,5-triazine and pharmaceutically acceptable acid addition salts thereof in finely pulverized form so that the average particle diameter is 20 microns or less have been found to be particularly useful for the treatment of peptic ulcers. When administered to humans in need thereof, 1 to 4 mg per day has been found effective.

24 Claims, 1 Drawing Figure

THE AXIS OF ABSCISSA & THE ORDINATE ARE ADMINISTRATION DATES & BODY WEIGHTS, RESPECTIVELY. •——• MEANS CONTROL GROUPS. X----X MEANS FINELY POWDERED GROUPS ACCORDING TO THIS INVENTION, & o··········o MEANS THE ORDINARY CONVENTIONAL POWER GROUPS.

LOW DOSAGE COMPOSITIONS OF FINELY PULVERIZED 2,4-DIAMINO-6-(2,5-DICHLOROPHENYL)-1,3,5-TRIAZINE AND PHARMACEUTICALLY ACCEPTABLE ACID ADDITION SALTS THEREOF AND ADMINISTRATION THEREOF

This is a continuation-in-part of our co-pending application Ser. No. 403,702 filed July 3, 1982, now U.S. Pat. No. 4,532,238.

2,4-diamino-6-(2,5-dichlorophenyl)-1,3,5-triazine and various acid addition salts thereof are known to exhibit strong anti-ulcer activity (see Japanese Pat. Nos. 9199103 and 1017236). However, in testing that compound for its anti-ulcer activity, it has been found that disadvantages arise due to lack of reproducibility of the level of anti-ulcer activity when the compound is administered without regard to the average particle size. In particular, it has been found that the compound lacks a dose dependency thereby giving rise to unpredictability as well as lack of reproducibility of the activity levels.

In our copending application Ser. No. 403,702, we described the surprising discovery that a number of advantages accrue from finely pulverizing 2,4-diamino-6-(2,5-dichlorophenyl)-1,3,5-triazine or a pharmaceutically acceptable acid addition salt thereof, so that the average particle diameter is 20 microns or less. A particularly useful average particle diameter is 5 to 10 microns and extremely good results have been achieved wherein the average particle diameter is about 8 microns.

When 2,4-diamino-6-(2,5-dichlorophenyl)-1,3,5-triazine or a pharmaceutically acceptable acid addition salt thereof is finely pulverized so that the average particle diameter is 20 microns or less, a number of quite unexpected advantages result. These advantages include a marked improvement in the properties and reproducibility of the activity. For example, the inhibition activity against stress ulcer in rats showed linear dose dependency.

In addition, quite surprisingly, toxicity studies revealed that the finely pulverized particles were far less toxic than those of the prior art having an average particle diameter of about 50 microns. In addition, we have observed that body weight increase inhibition which is a main side effect of administration of the compound of our copending application or a pharmaceutically acceptable acid addition salt thereof, is only transient and moderate and the recovery is far faster than occurs when the prior art having an average particle diameter of about 50 microns is administered.

The invention of our copending application resided in the discovery of unexpected improvement in properties and decrease in side effects when 2,4-diamino-6-(2,5-dichlorophenyl)-1,3,5-triazine and pharmaceutically acceptable acid addition salts thereof are finely pulverized so that the average particle diameter is 20 microns or less. Also included within that application were pharmaceutical compositions useful for treating peptic ulcers in humans and animals which comprises 2,4-diamino-6-(2,5-dichlorophenyl)-1,3,5-triazine or a pharmaceutically acceptable acid addition salt thereof in finely pulverized form so that the average particle diameter is 20 microns or less, preferably 5–10 microns, in combination with a pharmaceutically acceptable carrier.

According to a further embodiment in that application, the compound may be used in the form of its maleate salt. Both the compound and pharmaceutically acceptable acid addition salts thereof were found to be particularly useful when the average particle diameter is about 8 microns. Also included within our copending application was the method of treating peptic ulcers in humans and animals which comprises administering to a human or animal in need thereof a therapeutically effective amount of 2,4-diamino-6-(2,5-dichlorophenyl)-1,3,5-triazine or a pharmaceutically acceptable acid addition salt thereof, in finely pulverized form, so that the average particle diameter is 20 microns or less, preferably 5 to 10 microns, in combination with a pharmaceutically acceptable carrier. The compound may be administered as such or in the form of a pharmaceutically acceptable acid addition salt. The maleate salt was found to be particularly useful. The compounds and the pharmaceutically acceptable acid addition salts thereof, having an average particle diameter of about 8 microns, were shown to be useful in our copending application.

The advantages of our earlier invention were demonstrated when 2,4-diamino-6-(2,5-dichlorophenyl)-1,3,5-triazine was administered orally to rats and its activity on ulcer formation induced by stress was measured by the immobilization-water immersion method. According to that test, when the compound of our earlier invention was administered, a dosage of 1 mg/kg was effective, whereas when the compound had an average particle diameter of about 50 microns, a dosage of 5 mg/kg was shown to be ineffective. Similar results were obtained using the maleate salt according to the present invention. Table 1 below shows the lack of uniformity of result and linear dose dependency when the compound as known in the art having an average particle diameter of about 50 microns was administered to rats, as above described.

TABLE 1

| Dosages (mg/kg; per os) | Inhibition Rate | | |
|---|---|---|---|
| 0.37 | 37% | 46% | 29% |
| 1.12 | −9% | 29% | 42% |
| 3.72 | 62% | 47% | 33% |

Since 50 microns is a common particle diameter in pharmaceutical preparations, it was most surprising that such significant and important advantages resulted. Inhibition activity against stress ulcer in rats of the compound and pharmaceutically acceptable acid addition salts in the finely pulverized form are set forth in Table 2.

TABLE 2

| | Inhibition Rate | | | | |
|---|---|---|---|---|---|
| | 0.3 | 1.0 | 3.0 | 10 | 30 mg/kg |
| Substance (I) | 33% | 45% | 63% | 70% | 85% |
| Substance (II) | 35% | 51% | 70% | 85% | — |

The data shows linear dose dependency. ED$_{50}$ values can be determined as 1.22 mg/kg (per os) and 0.90 mg/kg (per os), respectively, for substance (I)-2,4-diamino-6-(2,5-dichlorophenyl)-1,3,5-triazine and for substance (II) which is the maleate salt thereof.

It was further quite unexpected to find that when 2,4-diamino-6-(2,5-dichlorophenyl)-1,3,5-triazine having an average particle diameter of about 8 microns was tested for toxicity, that on intraperitoneal injection, no rats were killed with dosages up to 3000 mg/kg while the same compound having an average particle diameter of about 50 microns showed an $LD_{50}$ of 1740 mg/kg (1614 to 1876) when injected intraperitoneally in male rats. A similar effect was observed with maleate salt according to the present invention. While the $LD_{50}$ of the maleate salt having an average particle diameter of 50 microns was determined to be 495 mg/kg (406 to 604), the maleate salt according to our copending application had an $LD_{50}$ of 835 mg/kg (696 to 1002). This decrease in toxicity is totally unexpected and represents a significant and important advance in the art.

The finely pulverized compound and pharmaceutically acceptable acid addition salts according to our copending application appeared to show decreased toxicity because the mechanism for achieving pharmacological and therapeutic activity and toxicity are quite distinct. The therapeutic results are achieved due to improved absorption, but the side effects most likely result from retention in the digestive tract.

A further advantage resulted from body weight increase inhibition which is one of the main side effects of the compound and salts of the present invention. When 10 mg/kg or more per day of either the compound or maleate salt was chronically administered to rats orally, body weight increase was inhibited. This is a side effect of triazines of this type. The inhibition is believed to be due to a decrease in food consumption and body weight is generally restored upon cessation of administration of the compound. However, when the compound or a pharmaceutically acceptable acid addition salt thereof according to our copending application having an average particle diameter of about 8 microns was administered, the appearance of the side effect was only transient and moderate and the recovery of body weight was far faster as compared to that occurring when the compound was administered having an average particle diameter of about 50 microns. The improvement was particularly dramatic when the maleate salt according to the present invention was compared with a maleate salt having an average particle diameter of about 50 microns, in accordance with the usual micron size for pharmaceuticals.

FIG. 1 shows a change in body weights which occurs on administration of 15 mg/kg per day to male rats (10 rats in one group) over a continuous 12 day period. The average particle sizes were 8 microns for the compound according our copending application as compared to the same compound having an average particle diameter of 50 microns.

2,4-diamino-6-(2,5-dichlorophenyl)-1,3,5-triazine and pharmaceutically acceptable acid addition salts thereof may be finely pulverized to achieve the average particle diameter of 20 microns or less by using jet Mill PJM-100NP (Nippon Newmatic MEG Co.). The pulverization is carried out by feeding 2 kg or less of the substance per hour. An average particle diameter of about 8 microns may be prepared in that manner. If necessary, auxiliary pulverizing agents such as starch, anhydrous silicic acid, etc. may be used. In measuring average particle size, the powder is dispersed in physiological saline solution containing one drop of Tween-80 with the aid of an ultrasonic homogenizer for 30 seconds and measured by Coleter Counter TA-II (Coulter Electronics Co., U.S.A.) equipped with aperture tube of 100 microns.

The compound and pharmaceutically acceptable acid addition salts according to our copending application may be formulated into tablets, sugar coated or otherwise, capsules, troches, pills, granules, powders, suppositories, emulsions, suspensions, syrups, and the like, using conventional pharmaceutical techniques. They may be administered one or more times daily as needed. Examples of auxiliary materials include:

(1) Fillers and diluents such as starch, lactose and mannitol;

(2) Binding agents such as microcrystalline cellulose, methyl-cellulose, other cellulose derivatives, gum arabic, gelatine, polyethylene glycol, polyvinyl alcohol, and polyvinyl pyrrolidone;

(3) Wetting agents such as glycerol;

(4) Disintegrating agents such as carboxymethyl cellulose (except sodium salt), microcrystalline cellulose, polyethylene glycol;

(5) Solubilization retarding agents such as carboxylmethyl cellulose sodium salt;

(6) Absorption accelerating agents such as quaternary ammonium compounds;

(7) Surface active agents such as cetyl alcohol, glycerine fatty acid esters;

(8) Fluidizing agents such as anhydrous silicic acid, synthetic aluminum silicate;

(9) Lubricants such as talc, magnesium stearate calcium stearate, solid polyethylene glycol; and

(10) Coating agents such as AEA (Trademark—Sankyo), MPM (Trademark—Tanabe), shellac, TC-5 (Trademark—Shin-Etsu).

Tablets, sugar coated tablets, capsules, troches, pills, etc. made from the present invention drugs may contain usual coating agents, etc. which possess untransparent agents therein. Such materials can, for example, be manufactured from polymers or from wax.

The pharmaceutical compositions of our copending application may be formulated into a sustained release form, either by micro-incapsulation or by other techniques known per se in the pharmaceutical industry.

Examples of suitable additives to prepare suppositories are water soluble bases such as polyethylene glycol and oil bases such as cacao butter, Witepsol (Trademark—Dynamite Nobel AG). Such bases may contain surface active agents therein.

Examples of materials used for the manufacture of suspension injections, emulsions, suspensions, syrups, etc. are as follows:

(1) Emulsification and suspension agents such as water, ethyl alcohol, isopropyl alcohol, ethyl carbonate, benzyl alcohol, benzyl benzoate, propylene glycol, 1,3-butylene glycol, dimethyl formamide, oils/fats, glycol, tetrahydrofurfuryl alcohol, polyethylene glycol;

(2) Surface active agents such as sorbitan fatty acid esters, polyoxyethylene sorbitan fatty acid esters, polyoxyethylene fatty acid esters, polyoxyethylene ethers of hydrogenated castor oil, lecithine;

(3) Suspension agents such as carboxymethyl cellulose sodium salt, methyl cellulose, other cellulose derivatives, tragacanth, gum arabic, other natural rubbers; and (4) Preservatives such as para-hydroxybenzoic acid esters, benzalconium chloride, sorbic acid salts.

The pharmaceutical compositions of our copending application may also contain the usual coloring agents, preservatives, perfumes, seasoning agents, sweetening agents and the like.

The pharmaceutical compositions described in our copending application contain from about 0.1% to 99.5% and more preferably from about 0.5 to 95% of 2,4-diamino-6-(2,5-dichlorophenyl)-1,3,5-triazine or a pharmaceutically acceptable acid addition salt thereof.

In the compositions described in our copending application, the compound or pharmaceutically acceptable acid addition salt thereof may be the sole therapeutic agent or the composition may contain other therapeutic agents such as digestive enzymes, antacids, inhibitors for stomach secretion, aromatic stomach agents, bitter stomach agents, protective agents for stomach mucous, anti-cholinic agents and the like. The compositions of our earlier application may also contain anti-inflammatory agents.

The present invention resides in our discovery that the finely pulverized 2,4-diamino-6-(2,5-dichlorophenyl)-1,3,5-triazine and pharmaceutically acceptable salts thereof having an average particle diameter of 20 microns or less as described in our co-pending application Ser. No. 403,702 are effective at quite unexpectedly low dosages when administered to humans for the treatment of ulcers. This was especially surprising because initial animal tests showed the triazine and its pharmaceutically acceptable salts to be much more effective than the larger particle diameter material of the prior art, but did not show any special effectiveness at low dosages.

It has now been discovered that on administration to humans the finely pulverized 2,4-diamino-6-(2,5-dichlorophenyl)-1,3,5-triazine or pharmaceutically acceptable salts thereof of our copending application are effective for the treatment of ulcers in humans when administered at dosages of 1 to 4 mg per day.

The present invention, therefore, resides in pharmaceutical compositions in unit dosage form for administration to humans containing 1 to 4 mg of finely pulverized 2,4-diamino-6-(2,5-dichlorophenyl)-1,3,5-triazine or pharmaceutically acceptable salts thereof having an average particle diameter of 20 microns or less in combination with a pharmaceutically acceptable carrier. Average particle diameters of 5 to 10 microns are preferred, especially about 8 microns.

The present invention also includes a method of treating ulcers in humans which comprises administering to a human in need thereof of 1 to 4 mg per day of 2,4-diamino-6-(2,5-dichlorophenyl)-1,3,5-triazine or a pharmaceutically acceptable salt thereof in finely pulverized form having an average particle diameter of 20 microns or less in combination with a pharmaceutically acceptable carrier. Preferably the average particle diameter is 5 to 10 microns, especially about 8 microns.

The pharmaceutical compositions and the production thereof described in our copending application are specifically incorporated herein by reference.

EXAMPLE 2,4-Diamino-6-(2,5-dichlorophenyl)-1,3,5-triazine is powdered by supplying it at a rate of not more than 2 kg/hour to a Jet Mill PJM-100 NP (Nippon Newmatic Mfg. Co.). The pulverized pharmaceutical is dispersed in a physiological saline solution containing one drop of Tween-80 by the use of ultrasonic homogenizer for 30 seconds and their particle diameter in average is measured by Coulter Counter TA-II (Coleter Eelectronics Co., USA) and the result is about 8 microns.

Data Showing Low Dosage Effectiveness

Clinical experiments were conducted wherein patients were given 1, 2 and 4 mg/day of 2,4-diamino-6-(2,5-dichlorophenyl)-1,3,5-triazine in separate groups. There were 133 patients participating in the group and 123 were separately analyzed (groups of 20, 46 and 57). The rate of recovery or cure of ulcers during those clinical trials over the period indicated was as follows:

| Period  | 1 mg/day | 2 mg/day | 4 mg/day |
| ------- | -------- | -------- | -------- |
| 4 weeks | 20.0%    | 17.4%    | 41.6%    |
| 8 weeks | 50.0%    | 47.8%    | 56.1%    |

It can be observed that the highest recovery rate was observed in the group receiving 4 mg per day, but there was a high recovery rate even at 1 mg/day.

There were imbalances between the hospitalized and outpatient distributions and the number of hospitalized patients in the 1 mg group was high, so the consideration was made by classifying the patients into hospitalized and out-patients. As far as the hospitalized patients were concerned, the 4 mg group showed marked superiority in all of the recovery rate of ulcer improvement, degree of ulcer, and effect against both subjective and non-subjective symptoms.

Only one side effect was noted. There was an increase in transaminase (GOT and GPT) observed in one case (1.8% of the total) in the 4 mg group.

What is claimed is:

1. A pharmaceutical composition in unit dosage form useful for the treatment of peptic ulcers in humans wherein each dosage unit comprises 1 to 4 mg of 2,4-diamino-6-(2,5-dichlorophenyl)-1,3,5-triazine or a pharmaceutically acceptable acid addition salt thereof in finely pulverized form so that the average particle diameter is 20 microns or less, in combination with a pharmaceutically acceptable carrier.

2. A composition according to claim 1 wherein the compound is in the form of the maleate salt.

3. A composition according to claim 1 wherein the average particle diameter is from 5 to 10 microns.

4. A composition according to claim 2 wherein the average particle diameter is from 5 to 10 microns.

5. A composition according to claim 1 wherein the average particle diameter is about 8 microns.

6. A composition according to claim 2 wherein the average particle diameter is about 8 microns.

7. A composition according to claim 1 wherein the compound is 2,4-diamino-6-(2,5-dichlorophenyl)-1,3,5-triazine and the average particle diameter is about 8 microns.

8. A composition according to claim 1 wherein each dosage unit contains 1 mg.

9. A composition according to claim 1 wherein each dosage unit contains 2 mg.

10. A composition according to claim 1 wherein each dosage unit contains 4 mg.

11. A composition according to claim 1 in oral administration form.

12. A composition according to claim 1 in rectal administration form.

13. A method of treating peptic ulcers in humans which comprises administering to a human in need thereof from 1 to 4 mg per day of 2,4-diamino-6-(2,5-dichlorophenyl)-1,3,5-triazine or a pharmaceutically acceptable acid addition salt thereof in finely pulverized form so that the average particle diameter is 20 microns or less, in combination with a pharmaceutically acceptable carrier.

14. A method according to claim 13 wherein the compound is in the form of the maleate salt.

15. A method according to claim 13 wherein the average particle diameter is 5 to 10 microns.

16. A method according to claim 14 wherein the average particle diameter is from 5 to 10 microns.

17. A method according to claim 13 wherein the average particle diameter is about 8 microns.

18. A method according to claim 14 wherein the average particle diameter is about B 8 microns.

19. A method according to claim 13 wherein the compound is 2,4-diamino-6-(2,5-dichlorophenyl)-1,3,5-triazine and the average particle diameter is about 8 microns.

20. A method according to claim 13 wherein 1 mg per day is administered.

21. A method according to claim 13 wherein 2 mg per day is administered.

22. A method according to claim 13 wherein 4 mg per day is administered.

23. A method according to claim 13 wherein the administration is oral.

24. A method according to claim 13 wherein the administration is rectal.

* * * * *